United States Patent [19]
Castro Pineiro et al.

[11] Patent Number: 6,150,391
[45] Date of Patent: Nov. 21, 2000

[54] DIAZABICYCLO-OCTANE DERIVATIVES AS 5-HT RECEPTOR LIGANDS

[75] Inventors: Jose Luis Castro Pineiro, Bishops Stortford; Michael Geoffrey Russell, Welwyn Garden City, both of United Kingdom

[73] Assignee: Merck Sharp & Dohme Ltd., Hoddesdon

[21] Appl. No.: 09/117,328

[22] PCT Filed: Jan. 21, 1997

[86] PCT No.: PCT/GB97/00181

§ 371 Date: Sep. 28, 1998

§ 102(e) Date: Sep. 28, 1998

[87] PCT Pub. No.: WO97/28162

PCT Pub. Date: Aug. 7, 1997

[30] Foreign Application Priority Data

Jan. 30, 1996 [GB] United Kingdom .................. 9601786

[51] Int. Cl.[7] ...................... A61K 31/4178; A61P 25/06; C07D 403/06
[52] U.S. Cl. .......................................... 514/397; 548/311.7
[58] Field of Search .......................... 548/311.7; 514/397

[56] References Cited

FOREIGN PATENT DOCUMENTS

WO95/32196  11/1995  WIPO .

OTHER PUBLICATIONS

Cram and Hammond, "Organic Chemistry", Mc–Graw Hill Book Co., NY, (1964) 2nd Ed., pp. 565–567.

*Primary Examiner*—Patricia L. Morris
*Attorney, Agent, or Firm*—James L. McGinnis; David L. Rose

[57] ABSTRACT

Compounds having formula I, or pharmaceutically acceptable salts or prodrugs thereof:

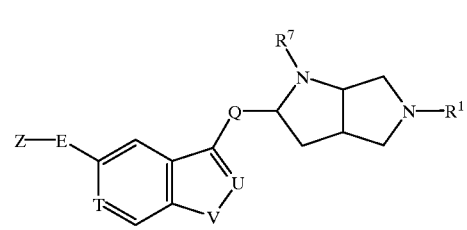

are selective agonists of the 5-$HT_{1D\alpha}$ receptor and are useful in the treatment of migraine and associated conditions.

9 Claims, No Drawings

DIAZABICYCLO-OCTANE DERIVATIVES AS 5-HT RECEPTOR LIGANDS

The present invention relates to a class of substituted 2,7-diazabicyclo[3.3.0]octane derivatives which act on 5-hydroxytryptamine (5-HT) receptors, being selective agonists of so-called "5-HT$_1$-like" receptors. They are therefore useful in the treatment of clinical conditions for which a selective agonist of these receptors is indicated.

It has been known for some time that 5-HT$_1$-like receptor agonists which exhibit selective vasoconstrictor activity are of use in the treatment of migraine (see, for example, A. Doenicke et al., *The Lancet*, 1988, Vol. 1, 1309–11; and W. Feniuk and P. P. A. Humphrey, *Drug Development Research*, 1992, 26, 235–240).

The human 5-HT$_{1D}$-like or 5-HT$_{1D}$ receptor has recently been shown by molecular cloning techniques to exist in two distinct subtypes. These subtypes have been termed 5-HT$_{1D_\alpha}$ (or 5-HT$_{1D-1}$) and 5-HT$_{1D_\beta}$ (or 5-HT$_{1D-2}$), and their amino acid sequences are disclosed and claimed in WO-A-91/17174.

The 5-HT$_{1D_\alpha}$ receptor subtype in humans is believed to reside on sensory terminals in the dura mater. Stimulation of the 5-HT$_{1D_\alpha}$ subtype inhibits the release of inflammatory neuropeptides which are thought to contribute to the headache pain of migraine. The human 5-HT$_{1D_\beta}$ receptor subtype, meanwhile, is located predominantly on the blood vessels and in the brain, and hence may play a part in mediating constriction of cerebral and coronary arteries, as well as CNS effects.

Administration of the prototypical 5-HT$_{1D}$ agonist sumatriptan (GR43175) to humans is known to give rise at therapeutic doses to certain adverse cardiovascular events (see, for example, F. Willett et al., *Br. Med. J.*, 1992, 304, 1415; J. P. Ottervanger et al., *The Lancet*, 1993, 341, 861–2; and D. N. Bateman, *The Lancet*, 1993, 341, 221–4). Since sumatriptan barely discriminates between the human 5-HT$_{1D_\alpha}$ and 5-HT$_{1D_\beta}$ receptor subtypes (cf WO-A-91/17174, Table 1), and since it is the blood vessels with which the 5-HT$_{1D_\beta}$ subtype is most closely associated, it is believed that the cardiovascular side-effects observed with sumatriptan can be attributed to stimulation of the 5-HT$_{1D_\beta}$ receptor subtype. It is accordingly considered (cf. G. W. Rebeck et al., *Proc. Natl. Acad. Sci. USA*, 1994, 91, 3666–9) that compounds which can interact selectively with the 5-HT$_{1D_\alpha}$ receptor subtype, whilst having a less pronounced action at the 5-HT$_{1D_\beta}$ subtype, might be free from, or at any rate less prone to, the undesirable cardiovascular and other side-effects associated with non-subtype-selective 5-HT$_{1D}$ receptor agonists, whilst at the same time maintaining a beneficial level of anti-migraine activity.

The compounds of the present invention, being selective 5-HT$_1$-like receptor agonists, are accordingly of benefit in the treatment of migraine and associated conditions, e.g. cluster headache, chronic paroxysmal hemicrania, headache associated with vascular disorders, tension headache and paediatric migraine. In particular, the compounds according to this invention are potent agonists of the human 5-HT$_{1D_\alpha}$ receptor subtype. Moreover, the compounds in accordance with this invention have been found to possess at least a 10-fold selective affinity for the 5-HT$_{1D_\alpha}$ receptor subtype relative to the 5-HT$_{1D_\beta}$ subtype, and they can therefore be expected to manifest fewer side-effects than those associated with non-subtype-selective 5-HT$_{1D}$ receptor agonists.

Several distinct classes of substituted five-membered heteroaromatic compounds are described in published European patent applications 0438230, 0494774 and 0497512, and published International patent applications 93/18029, 94/02477 and 94/03446. The compounds described therein are stated to be agonists of 5-HT$_1$-like receptors, and accordingly to be of particular use in the treatment of migraine and associated conditions. None of these publications, however, discloses nor even suggests the substituted 2,7-diazabicyclo[3.3.0]octane derivatives provided by the present invention.

In EP-A-0548813 is described a series of alkoxypyridin-4-yl and alkoxypyrimidin-4-yl derivatives of indol-3-ylalkylpiperazines which are alleged to provide treatment of vascular or vascular-related headaches, including migraine. There is, however, no disclosure nor any suggestion in EP-A-0548813 of replacing the substituted piperazine moiety with a differently substituted 2,7-diazabicyclo[3.3.0]octane moiety.

WO-A-91/18897 describes a class of tryptamine derivatives substituted by various five-membered rings, which are stated to be specific to a particular type of "5-HT$_1$-like" receptor and thus to be effective agents for the treatment of clinical conditions, particularly migraine, requiring this activity. A further class of tryptamine derivatives with alleged anti-migraine activity is disclosed in WO-A-94/02460. However, neither WO-A-91/18897 nor WO-A-94/02460 discloses or suggests the substituted 2,7-diazabicyclo[3.3.0]octane derivatives provided by the present invention.

Moreover, nowhere in the prior art mentioned above is there any disclosure of a subtype-selective 5-HT$_{1D}$ receptor agonist having a 5-HT$_{1D_\alpha}$ receptor binding affinity (IC$_{50}$) below 50 nM and at least a 10-fold selective affinity for the 5-HT$_{1D_\alpha}$ receptor subtype relative to the 5-HT$_{1D_\beta}$ subtype.

WO-A-95/32196 describes a class of substituted piperazine, piperidine and tetrahydropyridine derivatives as alpha subtype-selective agonists of the human 5-HT$_{1D}$ receptor. However, there is no disclosure nor any suggestion in WO-A-95/32196 of the substituted 2,7-diazabicyclo[3.3.0]octane derivatives provided by the present invention.

The compounds according to the present invention are subtype-selective 5-HT$_{1D}$ receptor agonists having a human 5-HT$_{1D_\alpha}$ receptor binding affinity (IC$_{50}$) below 50 nM, typically below 10 nM and preferably below 1 nM; and at least a 10-fold selective affinity, suitably at least a 50-fold selective affinity and preferably at least a 100-fold selective affinity, for the human 5-HT$_{1D_\alpha}$ receptor subtype relative to the 5-HT$_{1D_\beta}$ subtype. Moreover, the compounds in accordance with this invention possess interesting properties in terms of their efficacy and/or bioavailability.

The present invention provides a compound of formula I, or a salt or prodrug thereof:

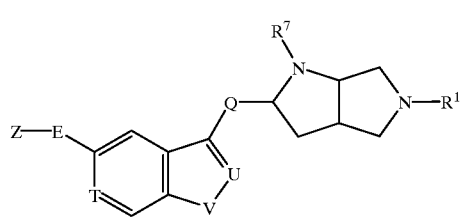

(I)

wherein

Z represents hydrogen, halogen, cyano, nitro, trifluoromethyl, —OR$^5$, —OCOR$^5$, —OCONR$^5$R$^6$, —OCH$_2$CN, —OCH$_2$CONR$^5$R$^6$, —SR$^5$, —SOR$^5$, —SO$_2$R$^5$, —SO$_2$NR$^5$R$^6$, —NR$^5$R$^6$, —NR$^5$COR$^6$, —NR$^5$CO$_2$R$^6$, —NR$^5$SO$_2$R$^6$, —COR$^5$, —CO$_2$R$^5$, —CONR$^5$R$^6$, or a group of formula (Za), (Zb), (Zc) or (Zd):

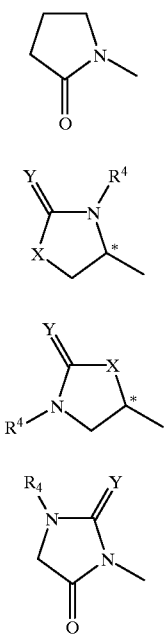

in which the asterisk * denotes a chiral centre; or

Z represents an optionally substituted five-membered heteroaromatic ring selected from furan, thiophene, pyrrole, oxazole, thiazole, isoxazole, isothiazole, imidazole, pyrazole, oxadiazole, thiadiazole, triazole and tetrazole;

X represents oxygen, sulphur, —NH— or methylene;

Y represents oxygen or sulphur;

E represents a chemical bond or a straight or branched alkylene chain containing from 1 to 4 carbon atoms;

Q represents a straight or branched alkylene chain containing from 1 to 6 carbon atoms, optionally substituted in any position by one or more substituents selected from fluoro and hydroxy;

T represents nitrogen or CH;

U represents nitrogen or C—$R^2$;

V represents oxygen, sulphur or N—$R^3$;

$R^1$ represents $C_{3-6}$ alkenyl, $C_{3-6}$ alkynyl, $C_{3-7}$ cycloalkyl $(C_{1-6})$alkyl, aryl$(C_{1-6})$alkyl or heteroaryl$(C_{1-6})$alkyl, any of which groups may be optionally substituted;

$R^2$, $R^3$, $R^4$ and $R^7$ independently represent hydrogen or $C_{r-6}$ alkyl; and $R^5$ and $R^6$ independently represent hydrogen, $C_{1-6}$ alkyl, trifluoromethyl, phenyl, methylphenyl, or an optionally substituted aryl$(C_{1-6})$alkyl or heteroaryl$(C_{1-6})$alkyl group; or $R^5$ and $R^6$, when linked through a nitrogen atom, together represent the residue of an optionally substituted azetidine, pyrrolidine, piperidine, morpholine or piperazine ring.

Where Z in the compounds of formula I above represents a five-membered heteroaromatic ring, this ring may be optionally substituted by one or, where possible, two substituents. As will be appreciated, where Z represents an oxadiazole, thiadiazole or tetrazole ring, only one substituent will be possible; otherwise, one or two optional substituents may be accommodated around the five-membered heteroaromatic ring Z. Examples of suitable substituents on the five-membered heteroaromatic ring Z include $C_{1-6}$ alkyl, $C_{2-6}$ alkenyl, $C_{2-6}$ alkynyl, $C_{3-7}$ cycloalkyl, aryl, aryl$(C_{1-6})$ alkyl, $C_{3-7}$ heterocycloalkyl, heteroaryl, heteroaryl$(C_{1-6})$ alkyl, $C_{1-6}$ alkoxy, $C_{1-6}$ alkylthio, amino, $C_{1-6}$ alkylamino, di$(C_{1-6})$alkylamino, halogen, cyano and trifluoromethyl.

The group $R^1$ may be optionally substituted by one or more substituents, as also may the groups $R^5$ or $R^6$ where these represent aryl$(C_{1-6})$alkyl or heteroaryl$(C_{1-6})$alkyl. Where $R^1$, $R^5$ or $R^6$ represents aryl$(C_{1-6})$alkyl or heteroaryl $(C_{1-6})$alkyl, any optional substitution will suitably be on the aryl or heteroaryl moiety thereof, although substitution on the alkyl moiety thereof is an alternative possibility. Examples of optional substituents thereon include halogen, cyano, trifluoromethyl, triazolyl, tetrazolyl, $C_{1-6}$ alkyl-tetrazolyl, hydroxy, keto, $C_{1-6}$ alkoxy, $C_{1-6}$ alkylthio, $C_{2-6}$ alkoxycarbonyl, $C_{2-6}$ alkylcarbonyl, $C_{1-6}$ alkylsulphonyl, arylsulphonyl, amino, $C_{1-6}$ alkylamino, di$(C_{1-6})$alkylamino, di$(C_{1-6})$alkylaminomethyl, $C_{2-6}$ alkylcarbonylamino, arylcarbonylamino, $C_{2-6}$ alkoxycarbonylamino, N-$(C_{1-6})$ alkyl-N-$(C_{2-6})$alkoxycarbonylamino, $C_{1-6}$ alkylsulphonylamino, arylsulphonylamino, $C_{1-6}$ alkylsulphonylaminomethyl, aminocarbonylamino, $C_{1-6}$ alkylaminocarbonylamino, di$(C_{1-6})$ alkylaminocarbonylamino, mono- or diarylaminocarbonylamino, pyrrolidinylcarbonylamino, piperidinylcarbonylamino, aminocarbonyl, $C_{1-6}$ alkylaminocarbonyl, di$(C_{1-6})$alkylaminocarbonyl, aminosulphonyl, $C_{1-6}$ alkylaminosulphonyl, di$(C_{1-6})$ alkylaminosulphonyl, aminosulphonylmethyl, $C_{1-6}$ alkylaminosulphonylmethyl and di$(C_{1-6})$ alkylaminosulphonylmethyl.

When $R^5$ and $R^6$, when linked through a nitrogen atom, together represent the residue of an azetidine, pyrrolidine, piperidine, morpholine or piperazine ring, this ring may be unsubstituted or substituted by one or more substituents. Examples of suitable substituents include $C_{1-6}$ alkyl, aryl $(C_{1-6})$alkyl, $C_{1-6}$ alkoxy, $C_{2-}$ alkoxycarbonyl and $C_{1-6}$ alkylaminocarbonyl. Typical substituents include methyl, benzyl, methoxy, methoxycarbonyl, ethoxycarbonyl and methylaminocarbonyl. In particular, where $R^5$ and $R^6$ together represent the residue of a piperazine ring, this ring is preferably substituted on the distal nitrogen atom by a $C_{2-6}$ alkoxycarbonyl moiety such as methoxycarbonyl or ethoxycarbonyl.

As used herein, the expression "$C_{1-6}$ alkyl" includes methyl and ethyl groups, and straight-chained or branched propyl, butyl, pentyl and hexyl groups. Particular alkyl groups are methyl, ethyl, n-propyl, isopropyl and tert-butyl. Derived expressions such as "$C_{1-6}$ alkoxy", "$C_{1-6}$ alkylthio" and "$C_{1-6}$ alkylamino" are to be construed accordingly.

The expression "$C_{2-6}$ alkenyl" as used herein refers to straight-chained and branched alkenyl groups containing from 2 to 6 carbon atoms. Typical examples include vinyl, allyl, dimethylallyl and butenyl groups.

The expression "$C_{2-6}$ alkynyl" as used herein refers to straight-chained and branched alkynyl groups containing from 2 to 6 carbon atoms. Typical examples include ethynyl and propargyl groups.

Typical $C_{3-7}$ cycloalkyl groups include cyclopropyl, cyclobutyl, cyclopentyl and cyclohexyl.

Typical $C_{3-7}$ cycloalkyl$(C_{1-6})$alkyl groups include cyclopropylmethyl and cyclohexylmethyl.

Typical aryl groups include phenyl and naphthyl.

The expression "aryl$(C_{1-6})$alkyl" as used herein includes benzyl, phenylethyl, phenylpropyl and naphthylmethyl.

Suitable heterocycloalkyl groups include azetidinyl, pyrrolidinyl, piperidinyl, piperazinyl and morpholinyl groups.

Suitable heteroaryl groups include pyridinyl, quinolinyl, isoquinolinyl, pyridazinyl, pyrimidinyl, pyrazinyl, pyranyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl and tetrazolyl groups.

The expression "heteroaryl($C_{1-6}$)alkyl" as used herein includes furylmethyl, furylethyl, thienylmethyl, thienylethyl, oxazolylmethyl, oxazolylethyl, thiazolylmethyl, thiazolylethyl, imidazolylmethyl, imidazolylethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyrimidinylmethyl, pyrazinylmethyl, quinolinylmethyl and isoquinolinylmethyl.

The term "halogen" as used herein includes fluorine, chlorine, bromine and iodine, especially fluorine.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in *Design of Prodrugs*, ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. For example, the compounds of formula I above wherein Z represents a group of formula (Zb) or (Zc) have a chiral centre denoted by the asterisk *, which may accordingly be in the (R) or (S) configuration. It is to be understood that all such isomers and mixtures thereof in any proportion are encompassed within the scope of the present invention.

In particular, the ring junction between the fused five-membered rings in the 2,7-diazabicyclo[3.3.0]octane moiety depicted in formula I is preferably in the cis configuration. Moreover, the relative stereochemistry between the carbon atoms at the ring junction and the carbon atom at the 3-position of the 2,7-diazabicyclo[3.3.0]octane moiety in formula I is preferably trans.

In summary, the compounds of formula I above preferably possess the relative stereochemistry depicted in formula IA as follows:

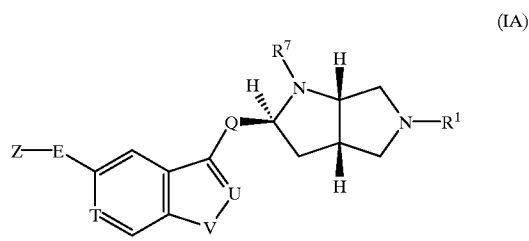

wherein Z, E, Q, T, U, V, $R^1$ and $R^7$ are as defined above.

Where E and Q, which may be the same or different, represent straight or branched alkylene chains, these may be, for example, methylene, ethylene, 1-methylethylene, propylene, 2-methylpropylene or butylene. In addition, the alkylene chain Q may be substituted in any position by one or more substituents selected from fluoro and hydroxy giving rise, for example, to a 2-hydroxypropylene, 2-hydroxymethyl- propylene, 2-fluoropropylene or 2-fluoromethyl-propylene chain Q. Moreover, E may represent a chemical bond such that the moiety Z is attached directly to the central fused bicyclic heteroaromatic ring system containing the variables T, U and V.

Suitably, E represents a chemical bond or a methylene linkage.

Suitably, Q represents a methylene linkage.

The compound of formula I in accordance with the present invention is suitably an indole, benzofuran or benzthiophene derivative of formula IB, an indazole derivative of formula IC, or a pyrrolo[2,3-c]pyridine derivative of formula ID:

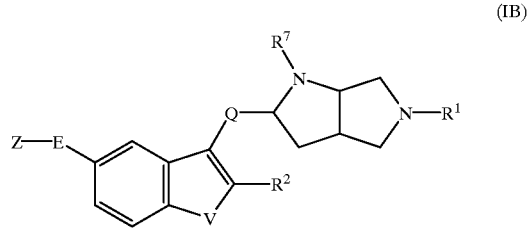

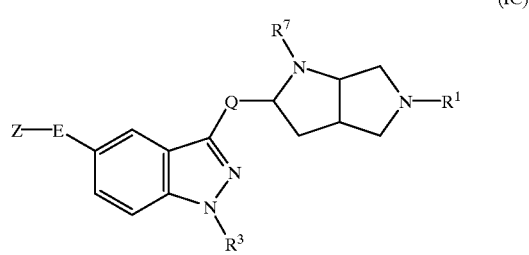

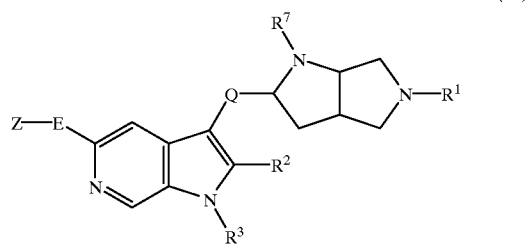

wherein Z, E, Q, V, $R^1$, $R^2$, $R^3$ and $R^7$ are as defined above. Preferably, the compounds according to the invention are indole or pyrrolo[2,3-c]pyridine derivatives of formula IE:

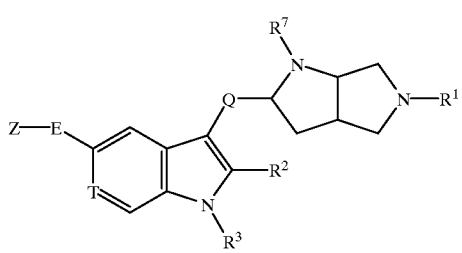

(IE)

wherein Z, E, Q, T, $R^1$, $R^2$, $R^3$ and $R^7$ are as defined above, in particular wherein $R^2$ and $R^3$ are both hydrogen.

Suitable values for the substituent $R^1$ include allyl, dimethylallyl, butenyl, propargyl, cyclohexylmethyl, benzyl, phenylethyl, phenylpropyl, furylmethyl, thienylmethyl, imidazolylmethyl and pyridylmethyl, any of which groups may be optionally substituted by one or more substituents selected typically from halogen, cyano, trifluoromethyl, triazolyl, tetrazolyl, $C_{1-6}$ alkyl-tetrazolyl, hydroxy, keto, $C_{1-6}$ alkoxy, amino, di($C_{1-6}$)alkylamino, di($C_{1-6}$)alkylaminomethyl, $C_{2-6}$ alkylcarbonylamino, $C_{2-6}$ alkoxycarbonylamino, N-($C_{1-6}$)alkyl-N-($C_{2-6}$)alkoxycarbonylamino, $C_{1-6}$ alkylsulphonylamino, aminocarbonylamino, aminocarbonyl, $C_{1-6}$ alkylaminocarbonyl, di($C_{1-6}$)alkylaminocarbonyl, aminosulphonyl and $C_{1-6}$ alkylaminosulphonylmethyl.

Particular values of $R^1$ include allyl, dimethylallyl, butenyl, propargyl, cyclohexylmethyl, benzyl, fluorobenzyl, difluorobenzyl, cyanobenzyl, tetrazolyl-benzyl, methyltetrazolyl-benzyl, methoxybenzyl, aminobenzyl, dimethylaminomethyl-benzyl, acetylamino-benzyl, aminocarbonyl-benzyl, methylaminocarbonyl-benzyl, dimethylaminocarbonyl-benzyl, aminosulphonyl-benzyl, phenylethyl, fluoro-phenylethyl, difluoro-phenylethyl, cyano-phenylethyl, trifluoromethyl-phenylethyl, triazolyl-phenylethyl, 2-hydroxy-1-phenylethyl, phenylcarbonylmethyl, amino-phenylethyl, dimethylamino-phenylethyl, acetylamino-phenylethyl, methoxycarbonyl-phenylethyl, (N-methyl-N-methoxycarbonyl)amino-phenylethyl, aminocarbonylamino-phenylethyl, 2-phenylpropyl, 3-phenylpropyl, furylmethyl, thienylmethyl, imidazolylmethyl, pyridylmethyl and amino-pyridylmethyl, especially benzyl, fluorobenzyl or fluoro-phenylethyl.

Suitably, $R^2$ and $R^3$ independently represent hydrogen or methyl, especially hydrogen.

Suitably, $R^4$ represents hydrogen or methyl.

Suitably, $R^5$ and $R^6$ are independently selected from hydrogen, methyl, ethyl, n-propyl, isopropyl, n-butyl, tert-butyl, trifluoromethyl, phenyl, methylphenyl (especially 4-methylphenyl), benzyl and phenethyl.

Suitably, $R^7$ represents hydrogen or methyl, especially methyl.

Suitably, the substituent Z represents hydrogen, fluoro, cyano, hydroxy, methoxy, ethoxy, benzyloxy, methylaminocarbonyloxy, cyano-methoxy, aminocarbonyl-methoxy, methylsulphonyl, aminosulphonyl, N-methylamino-sulphonyl, N,N-dimethylamino-sulphonyl, amino, formylamino, acetylamino, trifluoromethyl-carbonylamino, benzyloxy-carbonylamino, methyl-sulphonylamino, ethyl-sulphonylamino, methylphenyl-sulphonylamino, N-methyl-(N-methylsulphonyl)-amino, N-methyl-(N-ethylsulphonyl)-amino, N-methyl-(N-trifluoromethylsulphonyl)-amino, N-ethyl-(N-methylsulphonyl)-amino, N-benzyl-(N-methylsulphonyl)-amino, N-benzyl-(N-ethylsulphonyl)-amino, acetyl, methoxycarbonyl, ethoxycarbonyl, aminocarbonyl, methylaminocarbonyl, ethylaminocarbonyl, propylaminocarbonyl, butylaminocarbonyl, benzylaminocarbonyl or phenethyl-aminocarbonyl; or a group of formula (Za), (Zb), (Zc) or (Zd) as defined above; or an optionally substituted five-membered heteroaromatic ring as specified above.

In a particular embodiment, Z represents —$SO_2NR^5R^6$ in which $R^5$ and $R^6$ are as defined above. In a subset of this embodiment, $R^5$ and $R^6$ independently represent hydrogen or $C_{1-6}$ alkyl, especially hydrogen or methyl. Particular values of Z in this context include aminosulphonyl, N-methylamino-sulphonyl and N,N-dimethylamino-sulphonyl, especially N- methylamino-sulphonyl.

In another embodiment, Z represents a group of formula (Zb) in which $R^4$ is hydrogen or methyl. In a subset of this embodiment, X and Y both represent oxygen. In a particular aspect of this subset, the chiral centre denoted by the asterisk * is in the (S) configuration.

When the group Z represents an optionally substituted five-membered heteroaromatic ring, this is suitably a 1,3-oxazole, 1,3-thiazole, imidazole, 1,2,4-oxadiazole, 1,3,4-oxadiazole, 1,2,4-thiadiazole, 1,3,4-thiadiazole, 1,2,3-triazole, 1,2,4-triazole or tetrazole ring. Preferably, the ring is a 1,3-oxazole, 1,3-thiazole, imidazole, 1,2,4-oxadiazole, 1,2,4 -thiadiazole or 1,2,4-triazole ring, in particular an imidazol-1-yl, 1,2,4-triazol-1-yl or 1,2,4-triazol-4-yl moiety.

Suitably, the five-membered heteroaromatic ring Z is unsubstituted. Examples of optional substituents which may typically be attached to the moiety Z include methyl, ethyl, benzyl and amino.

A particular sub-class of compounds according to the invention is represented by the compounds of formula IIA with the relative stereochemistry as depicted below, and salts and prodrugs thereof:

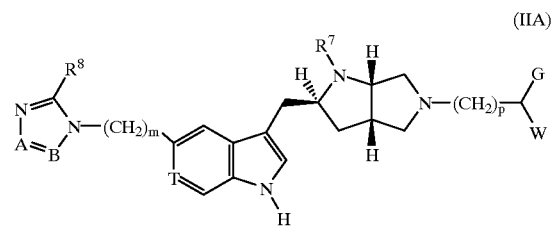

(IIA)

wherein m is zero, 1, 2 or 3, preferably zero or 1;

p is zero, 1 or 2;

T represents nitrogen or CH;

A represents nitrogen or CH;

B represents nitrogen or C—$R^9$;

$R^7$ is as defined with reference to formula I above;

$R^8$ and $R^9$ independently represent hydrogen, $C_{1-6}$ alkyl, $C_{2-6}$ alkenyl, $C_{3-7}$ cycloalkyl, aryl, aryl($C_{1-6}$)alkyl, $C_{3-7}$ heterocycloalkyl, heteroaryl, heteroaryl($C_{1-6}$)alkyl, $C_{1-6}$ alkoxy, $C_{1-6}$ alkylthio, amino, $C_{1-6}$ alkylamino, di($C_{1-6}$)alkylamino, halogen, cyano or trifluoromethyl;

G represents hydrogen, $C_{1-3}$ alkyl or hydroxy$(C_{1-3})$alkyl; and

W represents a group of formula (Wa), (Wb) or (Wc):

(Wa)

(Wb)

(Wc)

in which $W^1$ represents CH or nitrogen;

$W^2$ represents oxygen, sulphur, NH or N-methyl; and $R^{10}$ represents hydrogen, halogen, cyano, trifluoromethyl, triazolyl, tetrazolyl, $C_{1-6}$ alkyl-tetrazolyl, $C_{1-6}$ alkoxy, $C_{2-6}$ alkylcarbonyl, amino, $C_{1-6}$ alkylamino, di$(C_{1-6})$alkylamino, di$(C_{1-6})$alkylaminomethyl, $C_{2-6}$ alkylcarbonylamino, $C_{1-6}$ alkylsulphonylamino, aminocarbonylamino, $C_{1-6}$ alkylaminocarbonyl, aminosulphonyl or $C_{1-6}$ alkylaminosulphonylmethyl.

Particular values of $R^8$ and $R^9$ include hydrogen, methyl, ethyl, benzyl and amino, especially hydrogen.

Particular values of $R^{10}$ include hydrogen, fluoro, cyano, trifluoromethyl, triazolyl, tetrazolyl, methyl-tetrazolyl, methoxy, amino, dimethylaminomethyl, acetylamino, aminocarbonylamino, methylaminocarbonyl and aminosulphonyl, especially hydrogen or fluoro.

Particular values of G include hydrogen, methyl and hydroxymethyl.

Another sub-class of compounds according to the invention is represented by the compounds of formula IIB with the relative stereochemistry as depicted below, and salts and prodrugs thereof:

(IIB)

wherein m, p, T, G and W are as defined with reference to formula IIA above; and $R^5$, $R^6$ and $R^7$ are as defined with reference to formula I above.

Particular values of $R^5$ and $R^6$ in relation to formula IIB above include hydrogen and $C_{1-6}$ alkyl, especially hydrogen or methyl. Suitably, one of $R^5$ and $R^6$ represents hydrogen and the other represents hydrogen or methyl.

A further sub-class of compounds according to the invention is represented by the compounds of formula IIC with the relative stereochemistry as depicted below, and salts and prodrugs thereof:

(IIC)

wherein the asterisk * denotes a chiral centre;

m, p, T, G and W are as defined with reference to formula IIA above; and $R^4$, $R^7$ and Y are as defined with reference to formula I above.

Particular values of $R^4$ in relation to formula IIC include hydrogen and methyl.

Preferably, Y in formula IIC is oxygen.

Preferably, the chiral centre denoted by the asterisk * in formula IIC is in the (S) configuration.

Specific compounds within the scope of the present invention include:

(1RS, 3RS, 5RS)-7-benzyl-3-[5-(imidazol-1-yl)-1H-indol-3-ylmethyl]-2-methyl-2,7-diazabicyclo[3.3.0]octane;

(1RS,3RS,5RS)-7-[2-(3-fluorophenyl)ethyl]-2-methyl-3-[5-(1,2,4-triazol-4-yl)-1H-indol-3-ylmethyl]-2,7-diazabicyclo[3.3.0]octane;

(1RS, 3RS,5RS)-7-(4-fluorobenzyl)-2-methyl-3-[5-(1,2,4-triazol-4-yl)-1H-indol-3-ylmethyl]-2,7-diazabicyclo[3.3.0]octane; and salts and prodrugs thereof.

The invention also provides pharmaceutical compositions' comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former.

The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of migraine, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds according to the invention may be prepared by a process which comprises attachment of the $R^1$ moiety to a compound of formula III:

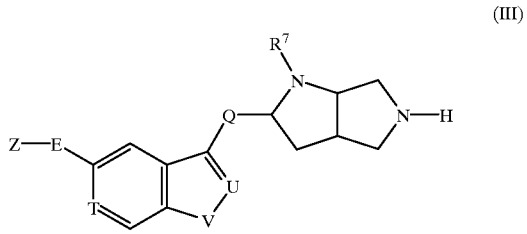

(III)

wherein Z, E, Q, T, U, V and $R^7$ are as defined above; by conventional means including N-alkylation.

Attachment of the $R^1$ moiety to the compounds of formula III may conveniently be effected by standard alkylation techniques. One example thereof comprises treatment with an alkenyl halide such as 4-bromobut-1-ene, 4-bromo-2-methylbut-2-ene or allyl bromide, an alkynyl halide such as propargyl bromide, or an aryl($C_{1-6}$)alkyl or heteroaryl($C_{1-6}$)alkyl halide such as benzyl iodide, typically under basic conditions, e.g. sodium hydride in N,N-dimethylformamide.

Alternatively, the $R^1$ moiety may conveniently be attached by reductive alkylation, which may be accomplished in a single step, or as a two-step procedure. The single-step approach suitably comprises treating the required compound of formula III as defined above with the appropriate aldehyde, e.g. benzaldehyde, 3-fluorophenylacetaldehyde, 4-fluorobenzaldehyde, pyridine carboxaldehyde, furfuraldehyde or thiophene carboxaldehyde, in the presence of a reducing agent such as sodium cyanoborohydride. In a typical two-step procedure, for the preparation of a compound of formula I wherein $R^1$ corresponds to a group of formula $—CH_2R^{11}$, a carboxylic acid derivative of formula $R^{11}—CO_2H$ is condensed with the required compound of formula III, suitably in the presence of 1-(3-dimethylaminopropyl)-3-ethylcarbodiimide hydrochloride and 1-hydroxybenzotriazole hydrate, to afford a compound corresponding to formula I wherein $R^1$ represents $—COR^{11}$; the carbonyl group thereof can then be reduced, for example by treatment with diisobutylaluminium hydride, and the required compound of formula I thereby obtained.

The compounds of formula III above wherein T represents CH, U represents $C—R^2$ and V represents $N—R^3$, corresponding to the indole derivatives of formula IE as defined above wherein T represents CH and $R^1$ is hydrogen, may be prepared by a process which comprises reacting a compound of formula IV:

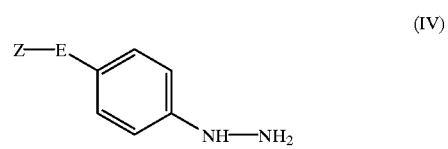

(IV)

wherein Z and E are as defined above; with a compound of formula V, or a carbonyl-protected form thereof:

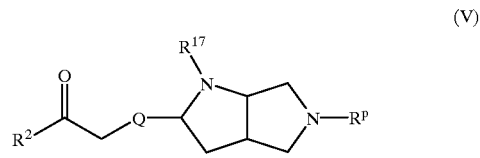

(V)

wherein $R^2$ and Q are as defined above, $R^P$ represents an amino-protecting group, and $R^{17}$ corresponds to the group $R^7$ as defined above or represents an amino-protecting group; followed, where required and in the appropriate order, by the following steps:

(a) removal of the amino-protecting group $R^{17}$;

(b) N-alkylation by standard methods to attach the moiety $R^7$ where this is other than hydrogen;

(c) N-alkylation by standard methods to attach the moiety $R^3$ where this is other than hydrogen; and (d) removal of the amino-protecting group $R^P$.

The reaction between compounds IV and V, which is an example of the well-known Fischer indole synthesis, is suitably carried out by heating the reagents together under mildly acidic conditions, e.g. 4% sulphuric acid at reflux.

Suitable carbonyl-protected forms of the compounds of formula V include the dimethyl acetal or ketal derivatives, and the 1,3-dioxan-2-yl derivatives.

The protecting group $R^P$ in the compounds of formula V is suitably a carbamoyl moiety such as ethoxycarbonyl or tert-butoxycarbonyl (BOC), which can conveniently be removed as necessary by treatment under acidic conditions. Indeed, the acidic conditions of the Fischer indole synthesis reaction will generally suffice to remove a BOC group,.

When $R^{17}$ in the compounds of formula V represents an amino-protecting group, this is suitably benzyl, which can conveniently be removed by conventional catalytic hydrogenation, or by transfer hydrogenation using a hydrogenation catalyst such as palladium on charcoal in the presence of a hydrogen donor such as ammonium formate.

Where $R^7$ is other than hydrogen, the moiety $R^7$ may be attached by standard N-alkylation methods. One such method is reductive alkylation, which involves treatment with the appropriate aldehyde or ketone in the presence of a reducing agent such as sodium cyanoborohydride.

The Fischer reaction between compounds IV and V may be carried out in a single step, or may proceed via an initial non-cyclising step at a lower temperature to give an intermediate of formula VI:

(VI)

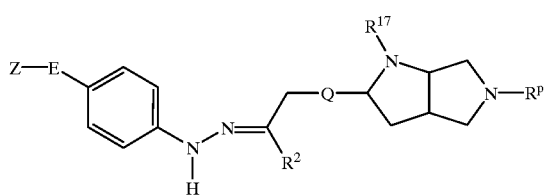

wherein Z, E, Q, $R^2$, $R^{17}$ and $R^P$ are as defined above; followed by cyclisation using a suitable reagent, e.g. a polyphosphate ester.

The compounds according to the invention wherein T represents CH, U represents $C-R^2$ and V represents $N-R^3$—i.e. the indole derivatives of formula IE as defined above wherein T represents CH—may alternatively be prepared by a process which comprises reacting a compound of formula IV as defined above with a compound of formula VII, or a carbonyl- protected form thereof:

(VII)

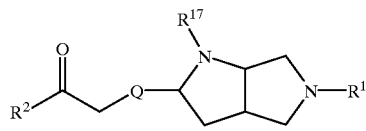

wherein Q, $R^1$, $R^2$ and $R^{17}$ are as defined above; under conditions analogous to those described above for the reaction between compounds IV and V; followed, where required and in the appropriate order, by the following steps:

(a) removal of the amino-protecting group $R^{17}$;
(b) N-alkylation by standard methods to attach the moiety $R^7$ where this is other than hydrogen; and
(c) N-alkylation by standard methods to attach the moiety $R^3$ where this is other than hydrogen.

As for the compounds of formula V, suitable carbonyl-protected forms of the compounds of formula VII include the dimethyl acetal or ketal derivatives, and the 1,3-dioxan-2-yl derivatives. Where the alkylene chain Q is substituted by a hydroxy group, this group may condense with the carbonyl moiety in compounds V and VII, whereby the carbonyl moiety is protected in the form of a cyclic hemiacetal.

As with that between compounds IV and V, the Fischer reaction between compounds IV and VII may be carried out in a single step, or may proceed via an initial non-cyclising step at a lower temperature to give an intermediate of formula VIII:

(VIII)

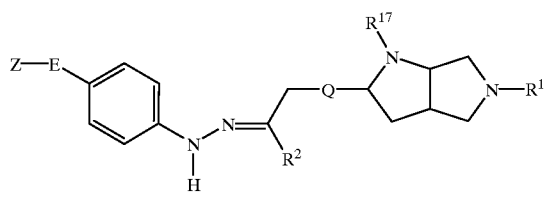

wherein Z, E, Q, $R^1$, $R^2$ and $R^{17}$ are as defined above; followed by cyclisation using a suitable reagent, e.g. a polyphosphate ester.

In a further procedure, the compounds of formula III above wherein T represents CH, U represents nitrogen and V represents $N-R^3$, corresponding to the indazole derivatives of formula IC as defined above wherein $R^1$ is hydrogen, may be prepared by a process which comprises cyclising a compound of formula IX:

(IX)

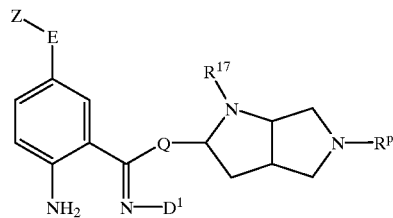

wherein Z, E, Q, $R^{17}$ and $R^P$ are as defined above, and $D^1$ represents a readily displaceable group; followed, where required and in the appropriate order, by the following steps:

(a) removal of the amino-protecting group $R^{17}$;
(b) N-alkylation by standard methods to attach the moiety $R^7$ where this is other than hydrogen;
(c) N-alkylation by standard methods to attach the moiety $R^3$ where this is other than hydrogen; and
(d) removal of the amino-protecting group $R^P$.

Similarly, the compounds of formula I wherein T represents CH, U represents nitrogen and V represents $N-R^3$—i.e. the indazole derivatives of formula IC as defined above—may be prepared by a process which comprises cyclising a compound of formula X:

(X)

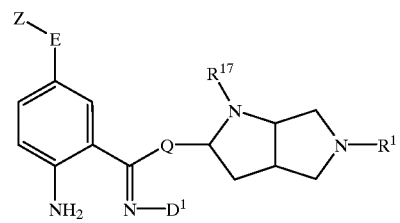

in which Z, E, Q, $R^1$, $R^{17}$ and $D^1$ are as defined above; followed, where required and in the appropriate order, by the following steps:

(a) removal of the amino-protecting group $R^{17}$;
(b) N-alkylation by standard methods to attach the moiety $R^7$ where this is other than hydrogen; and
(c) N-alkylation by standard methods to attach the moiety $R^3$ where this is other than hydrogen.

The cyclisation of compounds IX and X is conveniently achieved in a suitable organic solvent at an elevated temperature, for example in a mixture of m-xylene and 2,6-lutidine at a temperature in the region of 140° C.

The readily displaceable group $D^1$ in the compounds of formula IX and X suitably represents a $Cl_{-4}$ alkanoyloxy group, preferably acetoxy. Where $D^1$ represents acetoxy, the desired compound of formula IX or X may be conveniently prepared by treating a carbonyl compound of formula XI:

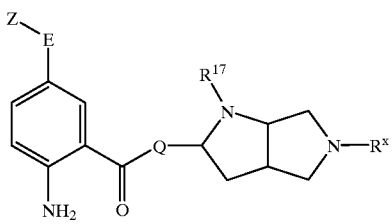

(XI)

wherein Z, E, Q and $R^{17}$ are as defined above, and $R^x$ corresponds to the group $R^1$ as defined above, or $R^x$ represents an amino-protecting group as defined for $R^pP$; or a protected derivative thereof, preferably the N-formyl protected derivative; with hydroxylamine hydrochloride, advantageously in pyridine at the reflux temperature of the solvent; followed by acetylation with acetic anhydride, advantageously in the presence of a catalytic quantity of 4-dimethylaminopyridine, in dichloromethane at room temperature.

The N-formyl protected derivatives of the intermediates of formula XI may conveniently be prepared by ozonolysis of the corresponding indole derivative of formula XII:

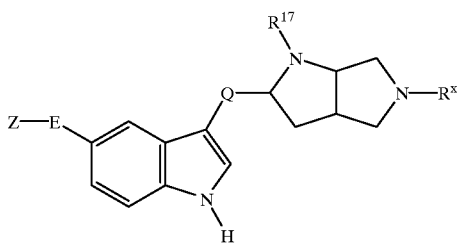

(XII)

wherein Z, E, Q, $R^{17}$ and $R^x$ are as defined above; followed by a reductive work-up, advantageously using dimethylsulphide.

The indole derivatives of formula XII may be prepared by methods analogous to those described in the accompanying Examples, or by procedures well known from the art.

In a still further procedure, the compounds of formula III above wherein T represents CH, U represents C—$R^2$ and V represents oxygen or sulphur, corresponding to the benzofuran or benzthiophene derivatives of formula IB wherein V is oxygen or sulphur respectively and $R^1$ is hydrogen, may be prepared by a process which comprises cyclising a compound of formula XIII:

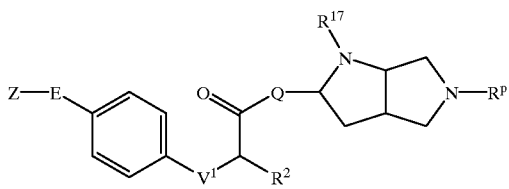

(XIII)

wherein Z, E, Q, $R^2$, $R^{17}$ and $R^p$ are as defined above, and $V^1$ represents oxygen or sulphur; followed, where required and in the appropriate order, by the following steps:

(a) removal of the amino-protecting group $R^{17}$;

(b) N-alkylation by standard methods to attach the moiety $R^7$ where this is other than hydrogen; and (c) removal of the amino-protecting group $R^p$.

Similarly, the compounds of formula I wherein T represents CH, U represents C—$R^2$ and V represents oxygen or sulphur—i.e. the benzofuran or benzthiophene derivatives of formula IB above—may be prepared by a process which comprises cyclising a compound of formula XIV:

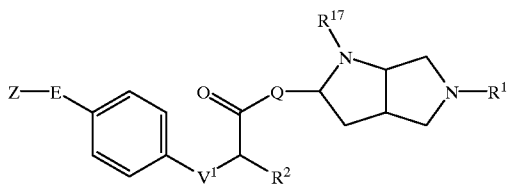

(XIV)

wherein Z, E, Q, $R^1$, $R^2$, $R^{17}$ and $V^1$ are as defined above; followed, where required, by the following steps:

(a) removal of the amino-protecting group $R^{17}$; and (b) N-alkylation by standard methods to attach the moiety $R^7$ where this is other than hydrogen.

The cyclisation of compounds XIII and XIV is conveniently effected by using polyphosphoric acid or a polyphosphate ester, advantageously at an elevated temperature.

The compounds of formula XIII and XIV may be prepared by reacting a compound of formula XV with a compound of formula XVI:

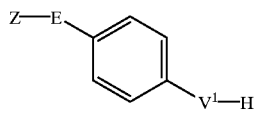

(XV)

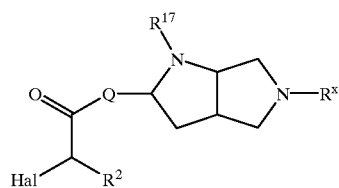

(XVI)

wherein Z, E, Q, $V^1$, $R^2$, $R^{17}$ and $R^x$ are as defined above, and Hal represents a halogen atom.

The reaction is conveniently effected in the presence of a base such as sodium hydroxide.

The hydroxy and mercapto derivatives of formula XV may be prepared by a variety of methods which will be readily apparent to those skilled in the art. One such method is described in EP-A-0497512.

The hydrazine derivatives of formula IV above may be prepared by methods analogous to those described in EP-A-0438230, EP-A-0497512, EP-A-0548813 and WO-A-91/18897.

Where they are not commercially available, the starting materials of formula V, VII and XVI may be prepared by methods analogous to those described in the accompanying Examples, or by standard procedures well known from the art.

It will be understood that any compound of formula I initially obtained from any of the above processes may, where appropriate, subsequently be elaborated into a further compound of formula I by techniques known from the art. For example, a compound of formula I wherein $R^1$ is benzyl initially obtained may be converted by catalytic hydrogenation to the corresponding compound of formula III, which in turn may be converted into a further compound of formula I using standard N-alkylation techniques as described above. Furthermore, a compound of formula I initially obtained wherein the $R^1$ moiety is substituted by nitro or cyano may be converted by catalytic hydrogenation to the corresponding amino- or aminomethyl-substituted compound respectively. Additionally, a compound of formula I wherein the $R^1$ moiety is substituted by hydroxy, possibly obtained by lithium aluminium hydride reduction of a precursor alkoxycarbonyl derivative, may be mesylated under standard conditions, and the mesyl group subsequently displaced by an amino moiety by treatment with the desired amine in a sealed tube at an elevated temperature. The amine derivative resulting from any of these procedures may then, for example, be N-acylated using the appropriate acyl halide, e.g. acetyl chloride: or aminocarbonylated, using potassium isocyanate, to the corresponding urea derivative; or converted to a 1,2,4-triazol-4-yl derivative using N,N-dimethylformamide azine; or reductively alkylated by treatment with the appropriate aldehyde or ketone in the presence of sodium cyanoborohydride. If desired, the amine derivative may also be carbamoylated by treatment with the requisite alkyl chloroformate. A compound of formula I initially obtained wherein the $R^1$ moiety is substituted by cyano may be converted, by treatment with sodium azide, to the corresponding tetrazole derivative, which in turn may be alkylated on the tetrazole ring by treatment with an alkyl halide under standard conditions. By way of additional illustration, a compound of formula I initially obtained wherein the $R^1$ moiety is substituted by an alkoxycarbonyl moiety may be saponified, by treatment with an alkali metal hydroxide, to the corresponding carboxy-substituted compound, which in turn may be converted to an amide derivative by treatment with the appropriate amine, advantageously in the presence of 1-(3-dimethylaminopropyl)-3-ethylcarboduimide hydrochloride and 1-hydroxybenzotriazole. Moreover, a compound of formula I wherein $R^3$ is hydrogen initially obtained may be converted into a compound of formula I wherein $R^3$ represents $C_{1-6}$ alkyl by standard alkylation techniques, for example by treatment with an alkyl iodide, e.g. methyl iodide, typically under basic conditions, e.g. sodium hydride in dimethylformamide, or triethylamine in acetonitrile.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds in accordance with the present invention potently and selectively bind to the $5\text{-HT}_{1D_\alpha}$ receptor subtype, inhibit forskolin-stimulated adenylyl cyclase activity, and stimulate $[^{35}S]$-GTPγS binding to membranes from clonal cell lines expressing human cloned receptors.

$5\text{-HT}_{1D_\alpha}/5\text{-HT}_{1D_\beta}$ Radioligand Binding

Chinese hamster ovary (CHO) clonal cell lines expressing the human $5\text{-HT}_{1D_\alpha}$ and $5\text{-HT}_{1D_\beta}$ receptors were harvested in PBS and homogenised in ice cold 50 mM Tris-HCl (pH 7.7 at room temperature) with a Kinematica polytron and centrifuged at 48,000 g at 4° C. for 11 min. The pellet was then resuspended in 50 mM Tris-HCl followed by a 10 min incubation at 37° C. Finally the tissue was recentrifuged at 48,000 g, 4° C. for 11 min and the pellet resuspended, in assay buffer (composition in mM: Tris-HCl 50, pargyline 0.01, $CaCl_2$ 4; ascorbate 0.1%; pH 7.7 at room temperature) to give the required volume immediately prior to use (0.2 mg protein/ml). Incubations were carried out for 30 min at 37° C. in the presence of 0.02–150 nM $[^3H]$-5-HT for saturation studies or 2–5 nM [3H]-5-HT for displacement studies. The final assay volume was 1 ml. 5-HT (10 $\mu$M) was used to define non-specific binding. The reaction was initiated by the addition of membrane and was terminated by rapid filtration through Whatman GF/B filters (presoaked in 0.3% PEI/0.5% Triton X) followed by 2×4 ml washings with 50 mM Tris-HCl. The radioactive filters were then counted on a LKB beta or a Wallac beta plate counter. Binding parameters were determined by non-linear, least squares regression analysis using an iterative curve fitting routine, from which $IC_{50}$ (the molar concentration of compound necessary to inhibit binding by 50%) values could be calculated for each test compound. The $IC_{50}$ values for binding to the $5\text{-HT}_{1D_\alpha}$ receptor subtype obtained for the compounds of the accompanying Examples were below 50 nM in each case. Furthermore, the compounds of the accompanying Examples were all found to possess a selective affinity for the $5\text{-HT}_{1D_\alpha}$ receptor subtype of at least 10-fold relative to the $5\text{-HT}_{1D_\beta}$ subtype.

$5\text{-HT}_{1D_\alpha}/5\text{-HT}_{1D_\beta}$ Adenylyl Cyclase Assay

Studies were performed essentially as described in *J. Pharmacol. Exp. Ther.*, 1986, 238, 248. CHO clonal cell lines expressing the human cloned $5\text{-HT}_{1D_\alpha}$ and $5\text{-HT}_{1D_\beta}$ receptors were harvested in PBS and homogenised, using a motor driven teflon/glass homogeniser, in ice cold Tris HCl-EGTA buffer (composition in mM: Tris HCl 10, EGTA 1, pH 8.0 at room temperature) and incubated on ice for 30–60 min. The tissue was then centrifuged at 20,000 g for 20 min at 4° C., the supernatant discarded and the pellet resuspended in Tris HCl-EDTA buffer (composition in mM: Tris HCl 50, EDTA 5, pH 7.6 at room temperature) just prior to assay. The adenylyl cyclase activity was determined by measuring the conversion of α-$[^{33}P]$-ATP to $[^{33}P]$-cyclic AMP. A 10 $\mu$l aliquot of the membrane suspension was incubated, for 10–15 min, in a final volume of 50 $\mu$l, at 30° C., with or without forskolin (10 $\mu$M), in the presence or absence of test compound. The incubation buffer consisted of 50 mM Tris HCl (pH 7.6 at room temperature), 100 mM NaCl, 30 $\mu$M GTP, 50 ,M cyclic AMP, 1 mM dithiothreitol, 1 mM ATP, 5 mM $MgCl_2$, 1 mM EGTA, 1 mM 3-isobutyl-1-methylxanthine, 3.5 mM creatinine phosphate, 0.2 mg/ml creatine phosphokinase, 0.5–1 $\mu$Ci α-$[^{33}P]$-ATP and 1 nCi

[$^3$H]-cyclic AMP. The incubation was initiated by the addition of membrane, following a 5 min preincubation at 30° C., and was terminated by the addition of 100 μl SDS (composition in mM: sodium lauryl sulphate 2%, ATP 45, cyclic AMP 1.3, pH 7.5 at room temperature). The ATP and cyclic AMP were separated on a double column chromatography system (*Anal. Biochem.*, 1974, 58, 541). Functional parameters were determined using a least squares curve fitting programme ALLFIT (*Am. J. Physiol.*, 1978, 235, E97) from which $E_{max}$ (maximal effect) and $EC_{50}$ (the molar concentration of compound necessary to inhibit the maximal effect by 50%) values were obtained for each test compound. Of those compounds which were tested in this assay, the $EC_{50}$ values for the 5-$HT_{1D_\alpha}$ receptor obtained for the compounds of the accompanying Examples were below 500 nM in each case. Moreover, the compounds of the accompanying Examples which were tested were all found to possess at least a 10-fold selectivity for the 5-$HT_{1D_\alpha}$ receptor subtype relative to the 5-$HT_{1D_\beta}$ subtype.

5-$HT_{1D_\alpha}$/5-$HT_{1D_\beta}$ GTPγS Binding

Studies were performed essentially as described in *Br. J. Pharmacol.*, 1993, 109, 1120. CHO clonal cell lines expressing the human cloned 5-$HT_{1D_\alpha}$ and 5-$HT_{1D_\beta}$ receptors were harvested in PBS and homogenised using a Kinematica polytron in ice cold 20 mM HEPES containing 10 mM EDTA, pH 7.4 at room temperature. The membranes were then centrifuged at 40,000 g, 4° C. for 15 min. The pellet was then resuspended in ice cold 20 mM HEPES containing 0.1 mM EDTA, pH 7.4 at room temperature and recentrifuged at 40,000 g, 4° C. for 15–25 minutes. The membranes were then resuspended in assay buffer (composition in mM: HEPES 20, NaCl 100, $MgCl_2$ 10, pargyline 0.01; ascorbate 0.1%; pH 7.4 at room temperature) at a concentration of 40 μg protein/ml for the 5-$HT_{1D_\alpha}$ receptor transfected cells and 40–50 μg protein/ml for the 5-$HT_{1D_\beta}$ receptor transfected cells. The membrane suspension was then incubated, in a volume of 1 ml, with GDP (100 μM for 5-$HT_{1D_\alpha}$ receptor transfected cells, 30 μM for the 5-$HT_{1D_\beta}$ receptor transfected cells) and test compound at 30° C. for 20 min and then transferred to ice for a further 15 min. [$^{35}$S]-GTPγS was then added at a final concentration of 100 pM and the samples incubated for 30 min at 30° C. The reaction was initiated by the addition of membrane and was terminated by rapid filtration through Whatman GF/B filters and washed with 5 ml water. The radioactive filters were then counted on a LKB beta counter. Functional parameters were determined by a non-linear, least squares regression analysis using an iterative curve fitting routine, from which $E_{max}$ (maximal effect) and $EC_{50}$ (the molar concentration of compound necessary to inhibit the maximal effect by 50%) values were obtained for each test compound. Of those compounds which were tested in this assay, the $EC_{50}$ values for the 5-$HT_{1D_\alpha}$ receptor obtained for the compounds of the accompanying Examples were below 500 nM in each case. Moreover, the compounds of the accompanying Examples which were tested were all found to possess at least a 10-fold selectivity for the 5-$HT_{1D_\alpha}$ receptor subtype relative to the 5-$HT_{1D_\beta}$ subtype.

EXAMPLE 1

(1RS,3RS,5RS)-7-Benzyl-3-[{5-(imidazol-1-yl)-1H-indol-3-yl}methy]-2-methyl-2,7-diazabicyclo[3.3.0]octane, oxalate Step 1: Ethyl 2-benzylamino-4-(1,3-dioxan-2-yl)butyrate To 60% NaH in oil (15.2 g, 0.38 mol) under argon was added anhydrous dimethylsulphoxide (300 mL) by cannula whilst stirring magnetically. The mixture was stirred at room temperature for 33 min. before adding by cannula, over 26 min., a solution of N-benzylidene glycine, ethyl ester (Stork, G.; Leong, A. Y. W.; Touzin, A. M. *J. Org. Chem.*, 1976, 41, 3491–3493) (66.2 g, 0.346 mol) in dimethylsulphoxide (200 mL). The resulting brown mixture was stirred at room temperature for 35 min. before adding by syringe, over 13 min., 2-(2-bromoethyl)-1,3-dioxane (56.6 mL, 0.415 mol). The mixture was stirred at room temperature for 2 h before partitioning between ice-water (1 L) and diethyl ether (1 L). The aqueous layer was reextracted with more diethyl ether (3×1 L) and the combined organic extracts were washed with saturated NaCl solution (300 mL), dried ($MgSO_4$) and evaporated in vacuo to leave 116.8 g of orange oil.

This crude product was dissolved in anhydrous 1,2-dichloroethane (1 L) and sodium triacetoxyborohydride (102.54 g, 0.484 mol) and glacial acetic acid (19.8 mL, 0.346 mol) was added. The mixture was stirred at room temperature under argon for 85 min. before quenching with saturated $NaHCO_3$ solution (1 L) and extracting with ethyl acetate (2 L+1 L). The combined organic extracts were dried (Na2SO4) and evaporated in vacuo. The residue was purified by flash chromatography (silica gel, 40–50% EtOAc/hexane) to give 77.3 g (73%) of the title compound as a yellow oil. $\delta_H$ (250 MHz, $CDCl_3$) 1.28 (3H, t, J=7.2 Hz), 1.32 (1H, m), 1.62–1.86 (4H, m), 2.05 (1H, m), 3.24 (1H, m), 3.64 (1H, d, J=13.0 Hz), 3.72 (2H, td, J=12.3 and 2.2 Hz), 3.83 (1H, d, J=13.0 Hz), 4.07 (2H, m), 4.18 (2H, q, J=7.2 Hz), 4.51 (1H, m), 7.22–7.36 (5H, m). m/e ($ES^+$) 308 $(M+H)^+$, 232 $(M-C_6H_5+2H)^+$.

Step 2: 2-Benzylamino-4-(1,3-dioxan-2-yl)butyric acid

A mixture of ethyl 2-benzylamino-4-(1,3-dioxan-2-yl)butyrate (77.5 g, 0.252 mol) and lithium hydroxide monohydrate (15.87 g, 0.378 mol) in tetrahydrofuran-methanol-water (1:3:1; 1 L) was stirred at room temperature for 3 days. The reaction mixture was concentrated in vacuo and the aqueous residue was diluted with water (200 mL), washed with diethyl ether (200 mL) and freeze dried. The residue was purified by flash chromatography (silica gel, 20–30% $MeOH/CH_2Cl_2$) to give 59.5 g (85%) of the title compound as a white solid. $\delta_H$ (360 MHz, $d_6$-$DMSO/D_2O$) 1.29 (1H, br d, J=13.4 Hz), 1.54 (2H, m), 1.63 (2H, m), 1.79 (1H, m), 3.05 (1H, t, J=6.0 Hz), 3.64 (2H, m), 3.80 (1H, d, J=13.1 Hz), 3.91–3.94 (3H, m), 4.44 (1H, t, J=5.1 Hz), 7.32–7.39 (5H, m), m/e ($ES^+$) 280 $(M+H)^+$, 204 $(M-C_6H_5+2H)^+$.

Step 3: (1RS,3RS,5RS)-2-Benzyl-3-[2-(1,3-dioxan-2-yl)ethyl]-2,7-diazabicyclo[3.3.0]octane-7-carboxylic acid, ethyl ester A mixture of N-allyl-N-(2-oxoethyl)carbamic acid, ethyl ester (Schenke, T.; Peterson, U. Eur. patent EPO393424A2, 1992) (0.203 g, 1.19 mmol) and 2-benzylamino-4-(1,3-dioxan-2-yl)butyric acid (0.330 g, 1.18 mmol) in anhydrous toluene (5 mL) was heated at reflux under argon for 24 h. After cooling, the solvents were removed in vacuo and the residue was purified by flash chromatography (silica gel, 50% EtOAc/petroleum ether) to give 0.3234 g (71%) of the title compound as a yellow oil. $\delta_H$ (360 MHz, $CDCl_3$) 1.26 (3H, m), 1.28–1.40 (2H, m), 1.48–1.89 (5H, m), 2.05 (1H, m), 2.69 (1H, m), 2.94 (1H, m), 3.10 (1H, m), 3.30–3.47 (4H, m), 3.58 (1H, m), 3.74 (2H, td), 3.92 (1H, d, J=13.6 Hz), 4.07–4.14 (4H, m), 4.48 (1H, t, J=5.0 Hz), 7.22–7.34 (5H, m). m/e ($ES^+$) 389 $(M+H)^+$.

Step 4: 4-(Imidazol-1-yl)nitrobenzene

To a stirred solution of imidazole (34.1 g, 0.50 mol) in DMF (300 ml) under Ar, was added portionwise, over 23 minutes, 60% NaH in oil (20.02 g, 0.50 mol). The mixture was then stirred at room temperature for 18 minutes before adding dropwise, over 40 minutes, a solution of 1-fluoro-4-nitrobenzene (70.62 g, 0.50 mol) in DMF (60 ml). The mixture was then stirred at room temperature overnight.

Water (600 ml) was then added and the solid was filtered off, washed with water, then stirred in boiling ethyl acetate (400 ml), allowed to cool and filtered, washing the solid with more ethyl acetate (50 ml), then petroleum ether (250 ml). The filtrate, now containing more solid, was refiltered and washed with petroleum ether. The combined solids were dried in a vacuum desiccator overnight to give 90.14 g (95%) of the title compound as a yellow solid. $\delta_H$ (360 MHz, DMSO-$d_6$) 7.59 (1H, t, J=1.1 Hz), 7.97–8.03 (3H, m), 8.38 (2H, d, J=9.2 Hz), 8.52 (1H, t).

Step 5: 4-(Imidazol-1-yl)aniline, dihydrochloride

A mixture of 4-(imidazol-1-yl)nitrobenzene (89.60 g, 0.474 mol) and 10% palladium on carbon (4.50 g) in ethanol (1200 ml) and 5N HCl (189 ml) was hydrogenated in two batches at 40 psi for 80 minutes. Water (450 ml) was then added to dissolve the product and the catalyst was removed by filtration, washing with more water, and the combined filtrates were evaporated in vacuo, using finally a freeze drier, to give 105.4 g (96%) of the title compound as a cream solid. $\delta_H$ (250 MHz, $D_2O$) 7.22 (2H, d, J=8.8 Hz), 7.35 (1H, t, J=2.1 Hz), 7.44 (2H, d, J=9.0 Hz), 7.59 (1H, t, J=1.8 Hz), 8.89 (1H, t, J=1.5 Hz).

Step 6: 4-(Imidazol-1-yl)phenylhydrazine, dihydrochloride

To a cooled (−15° C.) and stirred suspension of 4-(imidazol-1-yl)aniline, dihydrochloride (20 g, 86.2 mmol) in concentrated hydrochloric acid (100 ml) was added dropwise, over 1 hour, a solution of sodium nitrite (6.25 g, 90.6 mmol) in water (40 ml). After a further 10 minutes of stirring at −12° C., the mixture was quickly filtered to remove a solid, and the filtrate was added portionwise to a cooled (−20° C.) and stirred solution of tin (II) chloride dihydrate (100 g) in concentrated hydrochloric acid (50 ml) at such a rate as to maintain the internal temperature below −10° C. (15 minutes). The mixture was allowed to warm to 5° C. over 30 minutes, and the solid was collected and washed with diethyl ether (4×100 ml). The above solid was suspended in water (200 ml) and basified with 4N sodium hydroxide solution and extracted with ethyl acetate (5×500 ml). The combined organic solutions were dried ($Na_2SO_4$) and filtered. The filtrate was vigorously stirred while hydrogen chloride was being bubbled through the solution until a deep red mixture was obtained. Stirring was continued for a further 20 minutes to give a cream solid which was collected by filtration and dried over phosphorus pentoxide-potassium hydroxide under high vacuum to leave 12.7 g (60%) of the title compound; $\delta_H$ (360 MHz, DMSO-$d_6$) 7.20 (2H, d, J=9.0 Hz), 7.73 (2H, d, J=9.0 Hz), 7.91 (1H, t, J=1.5 Hz), 8.23 (1H, t, J=1.7 Hz), 9.71 (1H, t, J=1.3 Hz).

Step 7: (1RS,3RS,5RS)-2-Benzyl-3-[{5-(imidazol-1-yl)-1H-indol-3-yl]methyl}-2,7-diazabicyclo[3.3.0]octane-7-carboxylic acid, ethyl ester A mixture of (1RS,3RS,5RS)-2-benzyl-3-[2-(1,3-dioxan-2-yl)ethyl]-2,7-diazabicyclo[3.3.0]octane-7-carboxylic acid, ethyl ester (0.3081 g, 0.793 mmol) and 4-(imidazol-1-yl)phenylhydrazine, dihydrochloride (0.2055 g, 0.832 mmol) in 4% $H_2SO_4$ (aq) (10 mL) was heated at reflux under argon for 20 h whilst stirring magnetically. After cooling, the reaction mixture was made basic with 50% NaOH solution and extracted with EtOAc (4×25 mL). The combined organic extracts were dried ($K_2CO_3$) and evaporated in vacuo. The residue was purified by flash chromatography (silica gel, 2–4% MeOH/$CH_2Cl_2$) to give 0.1625 g (44%) of the title compound as a yellow gum. $\delta_H$ (250 MHz, $CDCl_3$) 1.23–1.26 (3H, m), 1.56–1.68 (1H, m), 1.92 (1H, m), 2.56 (1H, m), 2.79 (1H, m), 3.14 (1H, dd), 3.17–3.78 (7H, m), 4.07–4.13 (3H, m), 7.10–7.34 (11H, m), 7.74 (1H, s), 8.24 (1H, br s). m/e ($ES^+$) 470 (M+H)$^+$.

Step 8: (1RS, 3RS, 5RS)-3-[{5-(Imidazol-1-yl)-1H-indol-3-yl}methyl]-2,7-diazabicyclo[3.3.0]octane-7-carboxylic acid, ethyl ester A mixture of (1RS, 3RS, 5RS)-2-benzyl-3-[{5-(imidazol-1-yl)-1H-indol-3-yl}methyl]-2,7-diazabicyclo[3.3.0]octane-7-carboxylic acid, ethyl ester (0.1540 g, 0.328 mmol) and palladium hydroxide on carbon (0.1039 g) in ethanol (50 mL) was hydrogenated at 50 psi for 3 days. The catalyst was removed by filtration and the filtrate was evaporated in7 vacuo. The residue was dissolved in methanol (5 mL) and 5N HCl (aq) (72.1 μL, 0.361 mmol), ammonium formate (0.1041 g, 1.65 mmol) and 10%Pd/C (33.7 mg) was added. The mixture was heated at reflux under argon for 75 min., whilst stirring magnetically. The catalyst was removed by filtration and the filtrate was evaporated in vacuo. The residue was partitioned betwen 2N NaOH (aq) (20 mL) and $CH_2Cl_2$ (25 mL). The aqueous layer was reextracted with more $CH_2Cl_2$ (2×25 mL). The combined organic extracts were dried ($Na_2SO_4$) and evaporated in vacuo. The residue was purified by flash chromatography (silica gel, $CH_2Cl_2$—MeOH—$NH_3$ (aq); 95:5:0.5) to give 78.3 mg (63%) of the title compound as a colourless solid. $\delta_H$ (360 MHz, $CDCl_3$) 1.22 (3H, t, J=7.1 Hz), 1.69–1.75 (1H, m), 1.85 (1H, m), 2.83–2.90 (3H, m), 3.23 (1H, m), 3.32 (1H, m), 3.50–3.68 (3H, m), 3.94 (1H, m), 4.09 (2H, q, J=7.1 Hz), 7.17 (1H, dd, J=2.2 Hz), 7.19–7.22 (2H, m), 7.30 (1H, s), 7.43 (1H, d, J=8.4 Hz), 7.57 (1H, dd, J=1.9 Hz), 7.83 (1H, s), 8.37 (1H, br s). m/e ($ES^+$) 380 (M+H)$^+$.

Step 9: (1RS, 3RS,5RS)-3-[{5-(Imidazol-1-yl)-1H-indol-3-yl}methyl]-2-methyl-2,7-diazabicyclo[3.3.0]octane-7-carboxylic acid, ethyl ester To a solution of (1RS,3RS,5RS)-3-[{5-(imidazol-1-yl)-1H-indol-3-yl}methyl]-2,7-diazabicyclo[3.3.0]octane-7-carboxylic acid, ethyl ester (72.0 mg, 0.190 mmol) in anhydrous methanol (3 mL), under argon, was added glacial acetic acid (43.4 μL, 0.758 mmol), sodium cyanoborohydride (14.6 mg, 0.232 mmol) and 37% solution of formaldehyde in water (17.3 μL, 0.624 mmol). The mixture was then stirred at room temperature under argon for 2 h before quenching with saturated $K_2CO_3$ solution (1 mL). The mixture was partitioned between saturated $K_2CO_3$ solution (20 mL) and EtOAc (25 mL). The aqueous layer was reextracted with more EtOAc (25 mL) and the combined organic extracts were dried ($Na_2SO_4$) and evaporated in vacuo. The residue was purified by flash chromatography (silica gel, $CH_2Cl_2$—MeOH—$NH_3$ (aq); 95:5:0.5) to give 67.6 mg (91%) of the title compound as a colourless solid. $\delta_H$ (250 MHz, $CDCl_3$) 1.23 (3H, t, J=6.8 Hz), 1.65 (1H, m), 1.87–2.00 (1H, m), 2.53 (3H, s), 2.60 (1H, m), 2.82 (1H, m), 3.11–3.30 (4H, m), 3.41–3.46 (1H, m), 3.57 (1H, m), 3.79 (1H, m), 4.10 (2H, q, J=7.1 Hz), 7.14 (1H, d, J=2.2 Hz), 7.19–7.23 (3H, m), 7.30 (1H, t, J=1.2 Hz), 7.44 (1H, d, J=8.5 Hz), 7.53 (1H, d, J=2.0 Hz), 7.84 (1H, s), 8.37 (1H, br s). m/e ($ES^+$) 394 (M+H)$^+$.

Step 10: (1RS, 3RS,5RS)-7-Benzyl-3-[{5-(imidazol-1-yl)-1H-indol-3-yl}methyl]-2-methyl-2,7-diazabicyclo[3.3.0] octane, oxalate A solution of (1RS,3RS,5RS)-3-[{5-(imidazol-1-yl)-1H-indol-3-yl}methyl]-2-methyl-2,7-diazabicyclo[3.3.0] octane-7-carboxylic acid, ethyl ester (67.6 mg, 0.172 mol) in concentrated hydrochloric acid (2 mL) was heated at reflux for 48 h, whilst stirring magnetically. After cooling, the reaction mixture was carefully basified with 50% NaOH solution and extracted with $CH_2Cl_2$ (4×20 mL). The combined organic extracts were dried ($Na_2SO_4$) and evaporated in vacuo to leave 53.0 mg of yellow oil.

This crude product was dissolved in anhydrous methanol (3 mL) and benzaldehyde (20.9 μL, 0.206 mmol), glacial acetic acid (39.3 μL, 0.687 mmol) and sodium cyanoborohydride (14.7 mg, 0.234 mmol) were added. The mixture was stirred at room temperature under argon overnight before quenching with saturated $K_2CO_3$ solution (1 mL). The mixture was partitioned between saturated $K_2CO_3$ solution (10 mL) and EtOAc (20 mL). The aqueous layer was reextracted with more EtOAc (20 mL) and the combined organic extracts were dried ($Na_2SO_4$) and evaporated in vacuo. The residue was purified by flash chromatography (silica gel, $CH_2Cl_2$—MeOH—$NH_3$ (aq); 93:7:0.7) to give 46.2 mg (65%) of the title compound free base as an oil. The oxalate salt was prepared in methanol-diethyl ether; m.p. 100–105° C. Found: C, 57.57; H, 5.67; N, 10.42. $C_{26}H_{29}N_5$. 2.75 $C_2H_2O_4$. 0.23 $C_4H_{10}O$ requires: C, 57.59; H, 5.49; N, 10.36%. $\delta_H$ (360 MHz, $d_6$-DMSO) 1.71 (1H, m), 2.02 (1H, m), 2.44–2.50 (2H, m), 2.58 (1H, m), 2.83 (3H, s), 2.83–2.89 (1H, m), 2.96 (1H, m), 3.16 (1H, d, J=11.5 Hz), 3.30 (1H, m), 3.64 (2H, m), 3.88 (1H, m), 4.14 (1H, m), 7.20–7.26 (6H, mn), 7.36 (1H, dd, J=2.1 and 8.5 Hz), 7.42 (1H, d), 7.52 (1H, d, J=8.6 Hz), 7.74 (1H, s), 7.87 (1H, s), 8.30 (1H, s), 11.27 (1H, s). m/e (ES+) 412 (M+H)+.

EXAMPLE 2

(1RS,3RS,5RS)-7-(3-Fluorophenethyl)-2-methyl-3-[{5-(1,2,4-triazol-4-yl)-1H-indol-3-yl}methyl]-2,7-diazabicyclo[3.3.0]octane, oxalate Step 1: (1RS, 3RS, 5RS)-3-[{5-(1,2,4-triazol-4-yl)-1H-indol-3-yl}methyl]-2,7-diazabicyclo[3.3.0]octane-7-carboxylic acid, ethyl ester A mixture of (1RS, 3RS, 5RS)-2-benzyl-3-[2-(1,3-dioxan-2-yl)ethyl]-2,7-diazabicyclo[3.3.0]octane-7-carboxylic acid, ethyl ester (11.45 g, 29.5 mmol) and 4-(1,2,4-triazol-4-yl)phenylhydrazine (Matassa, V. G.; Reeve, A. J.; Street L. J. Br. patent GB2289464A, 1995) (5.42 g, 30.9 mmol) in 4% $H_2SO_4$ (aq) (400 mL) was heated at reflux under argon for 15 h, whilst stirring magnetically. After cooling the reaction mixture was made basic with 50% NaOH solution (60 mL) and extracted with EtOAc (4×400 mL). The combined organic extracts were dried ($K_2CO_3$) and evaporated in vacuo. The residue was purified by flash chromatography (silica gel, 3–7% MeOH/$CH_2Cl_2$) to give 5.67 g of orange solid.

This crude product was dissolved in methanol (150 mL) and 10% Pd/C (1.13 g), ammonium formate (3.79 g, 60.1 mmol) and 5N HCl (aq) (2.65 mL, 13.3 mmol) was added. The mixture was heated at reflux under argon for 100 min., whilst stirring magnetically. The catalyst was removed by filtration and the filtrate was evaporated in vacuo. The residue was partitioned between 2N NaOH solution (100 mL) and $CH_2Cl_2$ (100 mL). The aqueous layer was reextracted with more $CH_2Cl_2$ (7×100 mL). The combined organic extracts were dried (Na2SO4) and evaporated in vacuo. The residue was purified by flash chromatography (silica gel, $CH_2Cl_2$—MeOH—$NH_3$ (aq); 95:5:0.5 then 94:6:0.6) to give 1.6557 g (15%) of the title compound as a yellow brown solid. $\delta_H$ (360 MHz, $CDCl_3$) 1.22 (3H, t, J=7.1 Hz), 1.74 (1H, m), 1.86 (1H, mn), 2.90 (3H, m), 3.23 (1H, m), 3.36 (1H, m), 3.51–3.69 (3H, m), 3.97 (1H, m), 4.09 (2H, q, J=7.1 Hz), 7.16 (1H, m), 7.23 (1H, s), 7.48 (1H, d, J=8.5 Hz), 7.59 (1H, s), 8.46 (2H, s), 8.62 (1H, br s). m/e (ES+) 381 (M+H)+.

Step 2: (1RS 3RS,5RS)-2-Methyl-3-[{5-(1,2,4-triazol-4-yl)-1H-indol-3-yl}methyl]-2,7-diazabicyclo[3.3.0]octane-7-carboxylic acid, ethyl ester To a stirred solution of (1RS,3RS,5RS)-3-[{5-(1,2,4-triazol-4-yl)-1H-indol-3-yl}methyl]-2,7-diazabicyclo[3.3.0] octane-7-carboxylic acid, ethyl ester (1.6514 g, 4.34 mmol) in methanol (70 mL) was added glacial acetic acid (0.99 mL, 17.3 mmol), 37% solution of formaldehyde in water (0.423 mL, 5.64 mmol) and sodium cyanoborohydride (0.3309 g, 5.27 mmol). The mixture was stirred at room temperature under argon for 3.5 h before quenching with saturated $K_2CO_3$ solution (200 mL) and extracting with EtOAc (3×50 mL). The combined organic extracts were dried ($Na_2SO_4$) and evaporated in vacuo. The residue was purified by flash chromatography (silica gel, $CH_2Cl_2$—MeOH—$NH_3$ (aq); 95:5:0.5 then 94:6:0.6) to give 1.4723 g (86.0%) of the title compound as a cream solid. $\delta_H$ (250 MHz, $CDCl_3$) 1.23 (3H, t), 1.63 (1H, m), 1.84–1.96 (1H, m), 2.52 (3H, s), 2.59 (1H, m), 3.78 (1H, m), 4.10 (2H, q, J=7.0 Hz), 7.14–7.20 (2H, m), 7.50 (1H, d, J=12.6 Hz), 7.52 (1H, s), 8.48 (2H, s), 8.63 (1H, br s). m/e (ES+) 395 (M+H)+.

Step 3: (1RS,3RS,5RS)-2-Methyl-3-[{5-(1,2,4-triazol-4-yl)-1H-indol-3-yl}methyl]-2,7-diazabicyclo[3.3.0]octane A solution of (1RS,3RS,5RS)-2-methyl-3-[{5-(1,2,4-triazol-4-yl)-1H-indol-3-yl}methyl]-2,7-diazabicyclo[3.3.0] octane-7-carboxylic acid, ethyl ester (0.3452 g, 0.875 mmol) in concentrated hydrochloric acid (10 mL) was heated at reflux for 40 h, whilst stirring magnetically. After cooling, the reaction mixture was basified with 50% NaOH solution (8 mL) and extracted with $CH_2Cl_2$ (4×75 mL). The combined organic extracts were dried ($Na_2SO_4$) and evaporated in vacuo. The residue was purified by flash chromatography (alumina, $CH_2Cl_2$—MeOH—$NH_3$ (aq); 90:10:1) to give 0.2367 g (84%) of the title compound as a yellow gum. $\delta_H$ (360 MHz, $CDCl_3$) 1.42 (1H, m), 1.87 (1H, m), 2.43–2.59 (2H, m), 2.54 (3H, s), 2.66 (1H, d, J=11.1 Hz), 2.77 (1H, m), 2.81–2.86 (1H, m), 2.99 (1H, m), 3.13 (1H, dd, J=3.7 and 14.2 Hz), 3.29 (1H, m), 3.46 (1H, m), 7.14–7.17 (2H, m), 7.49 (1H, d, J=8.4 Hz), 7.52 (1H, d, J=2.0 Hz), 8.47 (2H, s), 8.58 (1H, br s). m/e (ES+) 323 (M+H)+.

Step 4: 1-(3-Fluorophenyl)-2-methoxyethene

Phenyllithium (98.3 ml of a 1.8M solution in cyclohexane/diethyl ether, 177 mmol) was added to a stirred suspension of (methoxymethyl)triphenylphosphonium chloride (60.82 g, 177 mmol) in diethyl ether (500 ml) at 0° C. under nitrogen. The solid was seen to dissolve and a bright orange/brown coloration formed. The mixture was stirred at 0° C. for 0.25 h and then at room temperature for 0.5 h. The mixture was cooled to −20° C. and 3-fluorobenzaldehyde (20.0 g, 161 mmol) then added. The reaction mixture was allowed to warm to room temperature and stirred overnight (16 h). Saturated ammonium chloride solution (250 ml) was added and the aqueous separated and extracted further with diethyl ether (x2). The combined ethereal layers were dried ($MgSO_4$), evaporated in vacuo and the residue distilled (≈60° C. at 1.3 mbar) to remove the majority of the phosphorous by-products. The distillate was then purified by column chromatography on silica gel, eluting with ethyl acetate/hexane (2:98) to give the title-enol ether as an E/Z mixture (10.7 g, 44%), δ (250 MHz,$CDCl_3$) 3.69 and 3.80 (total 3H, 2 of s, $OCH_3$), 5.21 and 5.77 (total 1H, 2 of d, J=7.0 Hz and 13.0 Hz respectively, C=CHz and C=$CH_E$), 6.18 (d, J=7.0 Hz, C=CHz), 6.78–7.41 (m, Ar—H and C=CHE).

Step 5: 3-Fluorophenylacetaldehyde

Concentrated hydrochloric acid (45 ml) was added to a stirred solution of the preceding enol ether (7.22 g, 47.5 mmol), in THF (225 ml), at 0° C. The mixture was stirred under nitrogen for 0.3 h, at 0° C., and then at room temperature for 3 h. Water was added and the volatiles were evaporated in vacuo. The residue was taken up in diethyl ether and the organic layer separated, washed with water (x2), saturated sodium bicarbonate solution (x1) and water (x1), dried ($MgSO_4$) and evaporated in vacuo to afford the title-aldehyde (5.81 g, 89%), δ (250 MHz, CDCl₃) 3.71 (2H, d, J=2.2 Hz, CH₂), 6.93–7.39 (4H, m, Ar—H), 9.76 (1H, t, J=2.1 Hz, CHO). This material was used without further purification in the next step.

Step 6: (1RS, 3RS, 5RS)-7-(3-Fluorophenethyl)-2-methyl-3-[{5-(1,2,4-triazol-4-yl)-1H-indol-3-yl}methyl]-2,7-diazabicyclo[3.3.0]octane, oxalate To a stirred solution of (1RS,3RS,5RS)-2-methyl-3-[{5-(1,2,4-triazol-4-yl)-1H-indol-3-yl}methyl]-2,7-diazabicyclo[3.3.0]octane (0.1193 g, 0.370 mmol) in anhydrous methanol (6 mL) under argon was added a solution of 3-fluorophenylacetaldehyde (62.6 mg, 0.453 mmol) in anhydrous methanol (2 mL), glacial acetic acid (84.74 μL, 1.48 mmol) and sodium cyanoborohydride (29.4 mg, 0.468 mmol). The mixture was stirred at room temperature under argon for 20 h before quenching with saturated K₂CO₃ solution (1 mL). The mixture was partitioned between saturated K₂CO₃ solution (15 mL) and ethyl acetate (20 mL). The aqueous layer was reextracted with EtOAc (20 mL) and the combined organic extracts were dried (Na₂SO₄) and evaporated in vacuo. The residue was purified by flash chromatography (silica gel, CH₂Cl₂—MeOH—NH₃ (aq); 93:7:0.7 then 92:8:0.8) to give 0.1131 g (69%) of the title compound, free base. The oxalate salt was prepared in methanol-diethyl ether; mp 117–119° C. Found: C, 60.88; H, 5.99; N, 14.53. C₂₆H₂₉FN₆. 1.4C₂H₂O₄ requires: C, 60.62: H, 5.62; N, 14.73%. δ$_H$ (360 MHz, d₆-DMSO) 1.64 (1H, m), 1.96 (1H, m), 2.50–2.63 (3H, m), 2.71–2.79 (5H, m), 2.79 (3H, s), 2.95 (1H, m), 3.18–3.28 (2H, m), 3.51 (1H, m), 3.90 (1H, m), 6.96 (1H, m), 7.03–7.08 (2H, m), 7.23 (1H, q, J=6.9 Hz), 7.34–7.36 (2H, m), 7.53 (1H, d, J=8.6 Hz), 7.84 (1H, s), 9.02 (2H, s), 11.31 (1H, s). m/e (ES⁺) 445 (M+H)⁺.

EXAMPLE 3

(1RS,3RS, 5RS)-7-(4-Fluorobenzyl)-2-methyl-3-[{5-(1,2,4-triazol-4-yl)-1H-indol-3-yl}methyl]-2,7-diazabicyclo[3.3.0]octane, oxalate Using a similar procedure to that described in Example 2, step 6, (1RS,3RS,5RS)-2-methyl-3-[{5-(1,2,4-triazol-4-yl)-1H-indol-3-yl}methyl]-2,7-diazabicyclo[3.3.0]octane (0.1447 g, 0.449 mmol) was reacted with 4-fluorobenzaldehyde (57.8 μL, 0.539 mmol), glacial acetic acid (0.103 mL, 1.80 mmol) and sodium cyanoborohydride (33.8 mg, 0.538 mmol) in anhydrous methanol (8 mL) for 16h to give 0.1463 g (76%) of the title compound free base as a cream solid. The oxalate salt was prepared in methanol-dichloromethane-diethyl ether; mp 108–118° C. Found: C, 52.86; H, 5.33; N, 12.79. C₂₅H₂₇FN₆. 2C₂H₂O₄. 2.7H₂O requires C, 52.84; H, 5.57; N, 12.75%. 5H (360 MHz, d₆-DMSO) 1.70 (1H, m), 2.01 (1H, m), 2.43–2.57 (3H, m), 2.82 (3H, s), 2.82–2.88 (1H, m), 2.96 (1H, m), 3.13 (1H, d, J=11.1 Hz), 3.28 (1H, m), 3.61 (2H, m), 3.88 (1H, m), 4.12 (1H, m), 7.00–7.05 (2H, m), 7.28–7.32 (2H, m), 7.38 (1H, dd, J=2.1 and 8.6 Hz), 7.44 (1H, fine d), 7.54 (1H, d, J=8.5 Hz), 7.92 (1H, fine d), 9.04 (2H, s), 11.33 (1H, s). m/e (ES⁺) 431 (M+H)⁺.

What is claimed is:

1. A compound of formula I, or a pharmaceutically acceptable salt thereof:

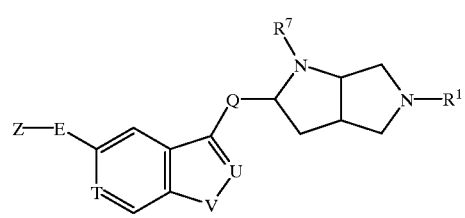

(I)

wherein

Z represents imidazole, optionally substituted with C₁₋₆ alkyl, C₂₋₆ alkenyl, C₂₋₆ alkynyl, C₃₋₇ cycloalkyl, aryl, aryl(C₁₋₆)alkyl, C₁₋₆ alkoxy, C₁₋₆ alkylthio, amino, C₁₋₆ alkylamino, di(C₁₋₆)alkylamino, halogen, cyano or trifluoromethyl, wherein aryl represents phenyl or naphthyl;

E represents a chemical bond or a straight or branched alkylene chain containing from 1 to 4 carbon atoms;

Q represents a straight or branched alkylene chain containing from 1 to 6 carbon atoms, optionally substituted in any position by one or more substituents selected from fluoro and hydroxy;

T represents CH;

U represents C—R²;

V represents N—R³;

R¹ represents C₃₋₆ alkenyl, C₃₋₆ alkynyl, C₃₋₇ cycloalkyl (C₁₋₆)alkyl, or aryl(C₁₋₆)alkyl, wherein aryl is phenyl or naphthyl, any of which groups may be optionally substituted with one or more substituents selected from halogen, cyano, trifluoromethyl, hydroxy, keto, C₁₋₆ alkoxy, amino, di(C₁₋₆)alkylamino, di(C₁₋₆) alkylaminomethyl, C₂₋₆ alkylcarbonylamino, C₂₋₆alkoxycarbonylamino, N-(C₁₋₆)alkyl-N-(C₂₋₆) alkoxycarbonylamino, C₁₋₆ alkylsulphonylamino, aminocarbonylamino, aminocarbonyl, C₁₋₆ alkylaminocarbonyl, di(C₁₋₆) alkylaminocarbonyl, aminosulphonyl, and C₁₋₆ alkylaminosulphonylmethyl; and R², R³, and R⁷ independently represent hydrogen or C₁₋₆ alkyl.

2. A compound as claimed in claim 1 possessing the relative stereochemistry depicted in formula IA below, or a pharmaceutically acceptable salt thereof:

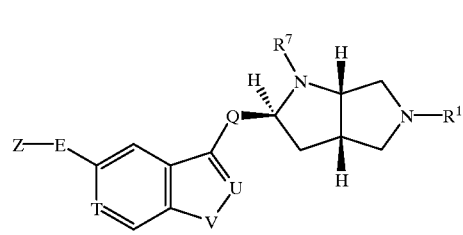

(IA)

wherein Z, E, Q, T, U, V, R¹ and R⁷ are as defined in claim 1.

3. A compound as claimed in claim 1 represented by formula IIA with the relative stereochemistry as depicted below, or a pharmaceutically acceptable salt thereof:

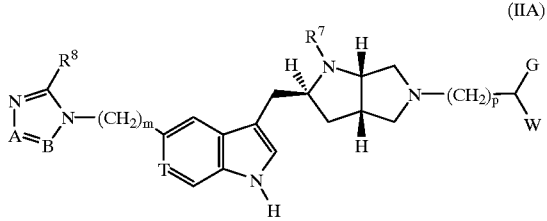 (IIA)

wherein
m is zero, 1, 2 or 3;
p is zero, 1 or 2;
T represents CH;
A represents CH;
B represents C—$R^9$;
$R^7$ is as defined in claim 1;
$R^8$ and $R^9$ independently represent hydrogen, $C_{1-6}$ alkyl, $C_{2-6}$ alkenyl, $C_{3-7}$ cycloalkyl, aryl, aryl($C_{1-6}$)alkyl, $C_{1-6}$ alkoxy, $C_{1-6}$ alkylthio, amino, $C_{1-6}$ alkylamino, di($C_{1-6}$)alkylamino, halogen, cyano or trifluoromethyl, wherein aryl represents phenyl or naphthyl;
G represents hydrogen, $C_{1-3}$ alkyl or hydroxy($C_{1-3}$)alkyl; and
W represents a group of formula (Wa):

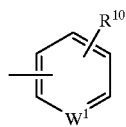 (Wa)

in which
$W^1$ represents CH; and
$R^{10}$ represents hydrogen, halogen, cyano, trifluoromethyl, $C_{1-6}$ alkoxy, $C_{2-6}$ alkylcarbonyl, amino, $C_{1-6}$ alkylamino, di($C_{1-6}$)alkylamino, di($C_{1-6}$)alkylaminomethyl, $C_{2-6}$ alkylcarbonylamino, $C_{1-6}$ alkylsulphonylamino, aminocarbonylamino, $C_{1-6}$ alkylaminocarbonyl, aminosulphonyl or $C_{1-6}$ alkylaminosulphonylmethyl.

4. The compound
(1RS,3RS,5RS)-7-benzyl-3-[5-(imidazol-1-yl)-1H-indol-3-ylmethyl]-2-methyl-2,7-diazabicyclo[3.3.0]octane;
or a pharmaceutically acceptable salt thereof.

5. A pharmaceutical composition comprising a compound of formula I as defined in claim 1 or a pharmaceutically acceptable salt thereof in association with a pharmaceutically acceptable carrier.

6. A method for the treatment of migraine, which method comprises administering to a patient in need of such treatment an effective amount of a compound of formula I as defined in claim 1 or a pharmaceutically acceptable salt thereof.

7. A pharmaceutical composition comprising a compound of claim 4 or a pharmaceutically acceptable salt thereof in association with a pharmaceutically acceptable carrier.

8. A method for the treatment of migraine, cluster headache, chronic paroxysmal hemicrania, vascular headache, tension headache, and pediatric migraine, which method comprises administering to a patient in need of such treatment an effective amount of a compound of formula I as defined in claim 1 or a pharmaceutically acceptable salt thereof.

9. A method for the treatment of migraine, cluster headache, chronic paroxysmal hemicrania, vascular headache, tension headache, and pediatric migraine, which method comprises administering to a patient in need of such treatment an effective amount of a compound of claim 4 or a pharmaceutically acceptable salt thereof.

* * * * *